United States Patent
Lewis et al.

(10) Patent No.: US 7,582,872 B2
(45) Date of Patent: Sep. 1, 2009

(54) VOLUMETRIC SPECTRAL IMAGING

(75) Inventors: E. Neil Lewis, Brookeville, MD (US); Donald Craig Lynch, Frederick, MD (US)

(73) Assignee: Malvern Instruments Incorporated, Southborough, MA (US)

(*) Notice: Subject to any disclaimer, the term of this patent is extended or adjusted under 35 U.S.C. 154(b) by 825 days.

(21) Appl. No.: 10/684,965

(22) Filed: Oct. 14, 2003

(65) Prior Publication Data

US 2004/0135086 A1 Jul. 15, 2004

Related U.S. Application Data

(60) Provisional application No. 60/417,820, filed on Oct. 11, 2002, provisional application No. 60/417,981, filed on Oct. 11, 2002.

(51) Int. Cl.
*G01J 5/02* (2006.01)
(52) U.S. Cl. .................................. 250/339.06
(58) Field of Classification Search ............... 250/341.1
See application file for complete search history.

(56) References Cited

U.S. PATENT DOCUMENTS

| | | | | |
|---|---|---|---|---|
| 5,094,786 | A * | 3/1992 | Nagashima et al. | 264/411 |
| 5,228,177 | A * | 7/1993 | Herzog et al. | 29/33 R |
| 5,679,954 | A * | 10/1997 | Soloman | 250/339.08 |
| 6,014,212 | A * | 1/2000 | Hammond et al. | 356/319 |
| 6,324,253 | B1 * | 11/2001 | Yuyama et al. | 378/57 |
| 6,537,826 | B1 * | 3/2003 | Horigane | 436/176 |
| 2002/0125434 | A1* | 9/2002 | Folestad et al. | 250/341.1 |
| 2004/0094715 | A1* | 5/2004 | Lewis | 250/339.02 |
| 2005/0090011 | A1* | 4/2005 | Du Plessis | 436/73 |
| 2006/0017922 | A1* | 1/2006 | Lewis et al. | 356/326 |
| 2006/0019409 | A1* | 1/2006 | Nelson et al. | 436/524 |

FOREIGN PATENT DOCUMENTS

SE 9402033 A * 12/1995
WO WO 0118527 A1 * 3/2001

* cited by examiner

*Primary Examiner*—David P Porta
*Assistant Examiner*—Kiho Kim
(74) *Attorney, Agent, or Firm*—Kristofer E. Elbing

(57) ABSTRACT

A spectral acquisition method includes actively processing a sample, such as a an opaque, friable pharmaceutical dosage unit, to expose characteristics of interior portions of the sample, and acquiring spectral information from the interior portions.

43 Claims, 4 Drawing Sheets

VOLUMETRIC SPECTRAL IMAGING

CROSS-REFERENCE TO RELATED APPLICATION

This application claims the benefit of U.S. Provisional Application Nos. 60/417,820 and 60/417,981, filed Oct. 11, 2002, and which are both herein incorporated by reference.

FIELD OF THE INVENTION

This invention relates to volumetric spectral imaging techniques, such as volumetric imaging techniques for use in pharmaceutical quality control determinations.

BACKGROUND OF THE INVENTION

It is known to use microtomes to cut thin sections of plant or animal material for microscopical observation. Microtomes typically consist of a knife, a block for supporting a specimen, and a device for moving the specimen relative to the knife.

SUMMARY OF THE INVENTION

Several aspects of the invention are presented in this application. These relate to improvements to spectral imaging techniques, such as volumetric pharmaceutical quality control determinations. In one general aspect, the invention features a spectral acquisition system that includes an exploration subsystem operative to expose interior portions of a three-dimensional sample, and a spectral acquisition subsystem operative to acquire images of the interior portions exposed by the exploration subsystem.

In preferred embodiments, the exploration subsystem can include a cutting implement and a guide. The exploration subsystem can include an actuator operative to advance the cutting implement. The exploration subsystem can be operative in the field of view of the spectral acquisition system. The system can further include a mechanical link, an electrical link, and a digital link between the exploration subsystem and the spectral acquisition system. The system can further include a control module operative to control the exploration subsystem and process information from the spectral acquisition system. The spectral acquisition system can include a two-dimensional array detector and a spectrally selective device. The spectral acquisition subsystem can operate in near-infrared or mid-infrared spectral regions. The system can further include an airborne waste collection system having an inlet proximate the exploration subsystem. The exploration subsystem can include a sample embedding substance.

In another general aspect, the invention features a spectral acquisition method that includes actively processing a sample to expose characteristics of interior portions of the sample, and acquiring spectral information from the interior portions of the sample exposed in the step of exposing.

In preferred embodiments, the steps of actively processing and acquiring can be applied to a friable material and the system can further include the step of preparing the friable material to withstand the step of actively processing before the step of actively processing. The steps of preparing, actively processing, and acquiring can be applied to a bulk pharmaceutical material. The steps of preparing, actively processing, and acquiring can be applied to a pharmaceutical dosage unit. The steps of preparing, actively processing, and acquiring can be applied to a pharmaceutical tablet including at least one active ingredient and one inert ingredient. The step of preparing can include fixing the sample in a fixing material and the step of actively processing includes cutting the sample. The method can further include repeating the steps of actively processing and acquiring to create a data set of information about different interior portions of the sample. The method can further include a step of selecting a spatial separation between the steps of actively processing to be on the same order as that of a spatial resolution of the step of acquiring. The method can further include a step of interpolating data received from the steps of acquiring to adjust for a spatial separation between the steps of actively processing. The steps of actively processing can expose planar interior surfaces. The step of actively processing and the step of acquiring can both take place with the sample in a position constrained in at least one dimension. The step of actively processing and the step of acquiring can both take place as part of an automated sequence. The method can further include steps of processing the spectral information acquired in the step of acquiring to obtain two-dimensional chemical image planes and reconstructing at least one three-dimensional image from the two dimensional chemical image planes. The step of acquiring can operate in near-infrared or mid-infrared spectral regions.

In a further general aspect, the invention features a spectral acquisition system that includes means for holding a friable pharmaceutical tablet, means for exposing interior portions of the friable pharmaceutical tablet, and means for obtaining spectral images of the exposed interior portions.

In preferred embodiments, the means for holding can include means for embedding the pharmaceutical tablet. The means for holding can include a holding wax. The means for exposing can include a cutting implement and a guide. The means for exposing can include means for advancing the cutting implement. The means for holding can be operative to hold the pharmaceutical tablet in a field of view of the means for obtaining spectral images during operation of the means for exposing. The system can further include a mechanical link, an electrical link, and a digital link between the means for exposing and the means for obtaining spectral images. The system can further include means for controlling the means for exposing and for processing information from the means for obtaining spectral images. The means for obtaining spectral images can operate in near-infrared or mid-infrared spectral regions. The system can further include means for collecting airborne waste from the means for exposing.

In another general aspect, the invention features a spectral acquisition method that includes positioning a pharmaceutical tablet within an optical field of view of an acquisition system, removing material from the tablet within the field of view, and acquiring an image of the tablet by the acquisition system after the step of removing.

In preferred embodiments, the steps of removing and acquiring can be applied to a friable tablet and the method can further include the step of preparing the friable tablet to withstand the step of removing. The steps of preparing, removing, and acquiring can be applied to a pharmaceutical tablet including at least one active ingredient and one inert ingredient. The step of preparing can include fixing the sample in a fixing material and the step of removing can include cutting the sample. The step of preparing can include fixing the sample in a fixing material and the step of removing can include cutting the sample with a blade. The step of preparing can include fixing the sample in a fixing material and the step of removing can include cutting the sample with a rotating blade. The method can further include repeating the steps of removing and acquiring to create a data set of information about different interior portions of the sample. The method can further include a step of selecting a spatial separation between the steps of removing to be on the same order as that of a spatial resolution of the step of acquiring. The method can further include a step of interpolating data received from the steps of acquiring to adjust for a spatial separation between the steps of removing. The step of removing and the step of acquiring can both take place with the sample in a position constrained in at least one dimension. The step of removing and the step of acquiring can both take place as part of an automated sequence. The method can further include steps of processing the spectral information acquired in the step of acquiring to obtain two-dimensional chemical image planes and reconstructing at least one three-dimensional image from the two dimensional chemical image planes. The method can further include the step of obtaining the tablet as a sample of a tablet making process, with the steps of obtaining, removing, and acquiring taking place as part of a quality control process for the tablet making process that includes further steps of obtaining, removing, and acquiring. The method can further include the step of obtaining the tablet from a formulation-phase experiment. The steps of removing and acquiring can take place as part of a root-cause analysis process. The step of acquiring an image can acquire an image in near-infrared or mid-infrared spectral regions. The step of acquiring can be operative to obtain an image reflected from a surface of the tablet exposed by the step of removing. The step of acquiring can be operative to obtain an image from material removed by the step of removing.

Systems according to the invention are beneficial in that they can allow for the efficient acquisition of information from interior regions of samples, such as opaque, friable pharmaceutical tablets.

DETAILED DESCRIPTION OF AN
ILLUSTRATIVE EMBODIMENT

Figure 1:
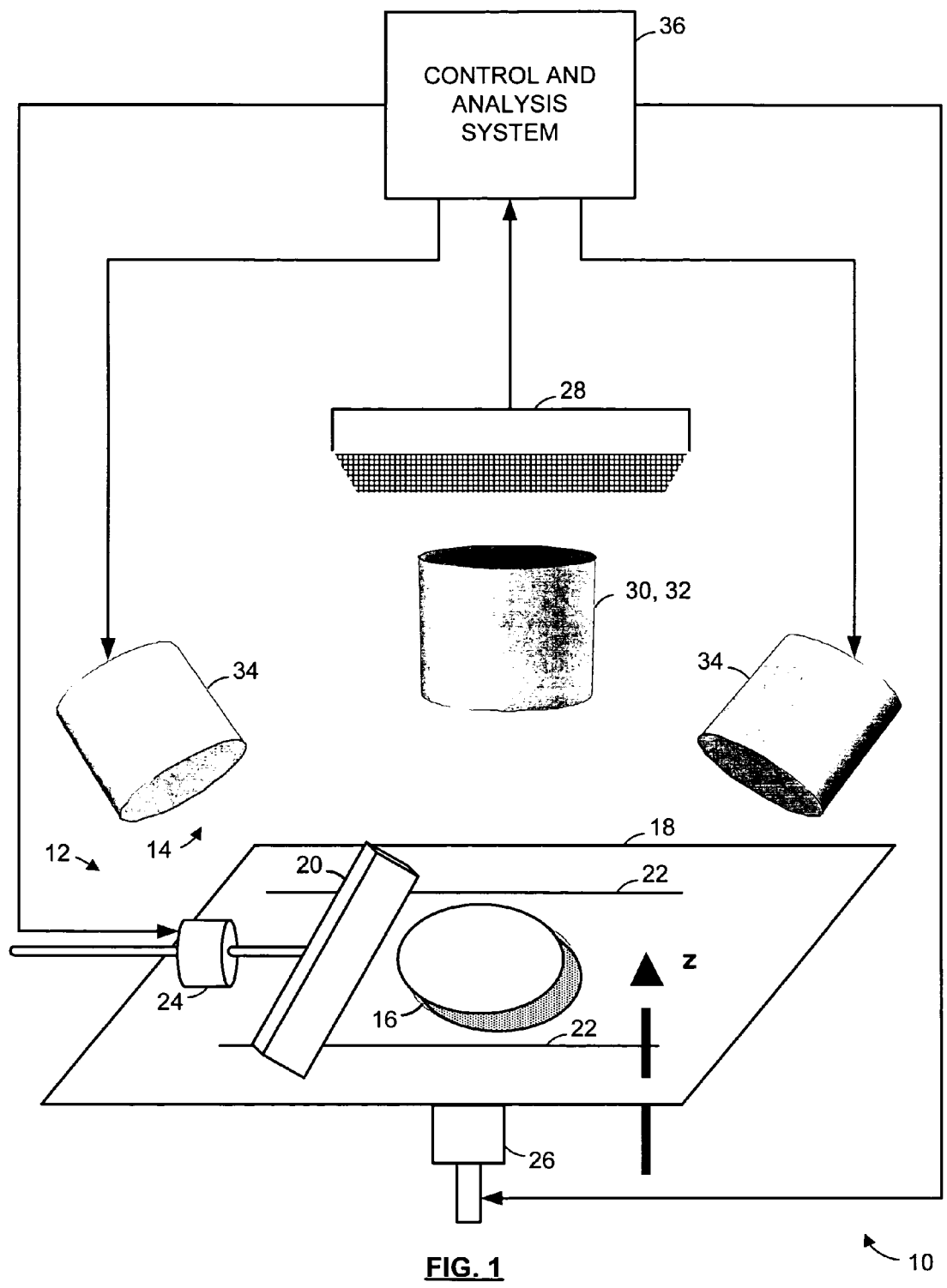
FIG. 1 is a block diagram illustrating a volumetric spectral imaging system according to the invention.

Referring to FIG. 1, an illustrative volumetric spectral imaging system 10 according to the invention includes a sample processing subsystem 12 and an acquisition subsystem 14. The sample processing subsystem is designed to cut away, alter, or otherwise actively explore part of a sample to expose interior portions of the sample that were not previously exposed. The acquisition subsystem is designed to acquire spectral information about a sample 16 from the interior portions exposed by the sample processing subsystem.

The sample processing subsystem 12 can include a processing surface, such as a cutting surface 18, which can be reflective. The cutting surface can be equipped with a sectioning blade 20 and guides 22 positioned to guide the blade through a sample volume along a path parallel with the cutting surface. The blade can be driven by hand or by an actuator 24 in such a way as to slice very thin slices of a sample in planes parallel to, but above, the cutting surface. Note that the cutting surface could also move with respect to a stationary blade, but this may introduce alignment errors between acquisitions. A sample well within the processing surface can be mounted on a micrometer or other actuator 26, which can advance the sample in a direction normal to the x-y plane of the cutting surface (i.e., in the z-direction). Of course, other mechanical arrangements could also be used to move the blade and sample relative to each other, such as moving the blade or moving the cutting surface.

The acquisition subsystem 14 includes a sensor and a spectrally selective element designed to acquire spectral information from the sample volume. This information is preferably acquired in the form of a two-dimensional near-infrared image, but some valuable information may also be available in other spectral regions, such as the mid-infrared, ultraviolet, or visible regions, and/or from one-dimensional or even point images. In the illustrative embodiment, the sensor is a near-infrared two-dimensional focal-plane array sensor 28 and the spectrally selective element is a tunable filter 30, such liquid crystal tunable filter (LCTF), which faces the sample volume. Imaging optics 32, such as a macroscopic or microscopic lens, are also provided between the sensor and the sample volume. One or more illumination sources 34 may also be provided to illuminate the sample.

The acquisition system in this embodiment allows for the efficient acquisition of a multispectral data set for each view of the sample. The acquisition subsystem can also be designed in accordance with, or otherwise combined with, the teachings of two previous applications entitled "Hybrid-Scanning Spectrometer" Ser. Nos. 09/817,785, and 09/828,281, filed on Mar. 26, 2001 and Apr. 6, 2001, respectively. The systems described in this application can also be combined with the teachings described in applications entitled "High-Volume On-Line Spectroscopic Composition Testing of Manufactured Pharmaceutical Dosage Units," including application Ser. No. 09/507,293, filed on Feb. 18, 2000, application No. 60/120,859, filed on Feb. 19, 1999, and application No. 60/143,801, filed on Jul. 14, 1999 (PCT/US00/19271 and PCT/US00/19273). The concepts presented in this application can further be combined with subject matter described in applications entitled "High-Throughput Infrared Spectrometry," including application Ser. No. 09/353,325, filed Jul. 14, 1999, application No. 60/092,769 filed on Jul. 14, 1998, and application No. 60/095,800 filed on Aug. 7, 1998 (PCT/US99/15900), as well as applications entitled "Multi-Source Array," including application No. 60/183,663, filed on Feb. 18, 2000, and application Ser. No. 09/788,316, filed on Feb. 16, 2001 (PCT/US01/05262). All of the applications listed in this paragraph are herein incorporated by reference.

Figure 2:
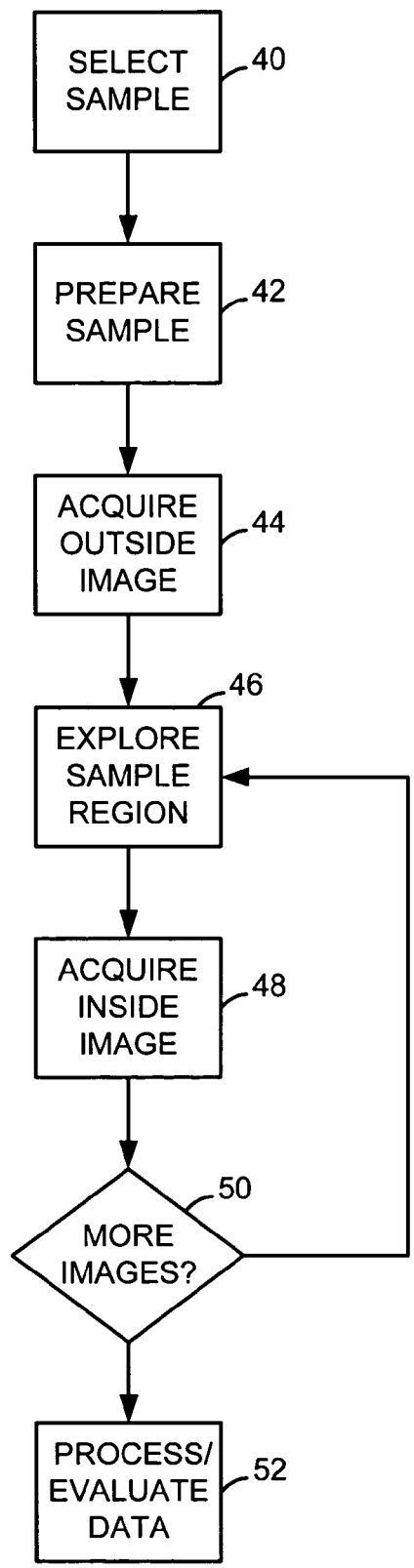
FIG. 2 is a flowchart illustrating the operation of the system of FIG. 1.

In operation, referring to FIG. 2, a sample is first selected (step 40). This selection process can be performed manually, randomly, or it may be the result of earlier characterizations of a sample population by this system or another.

The sample is then prepared for acquisition (step 42). This step preferably involves fixing of friable materials or materials that are otherwise incompatible with the sample processing technique used by the system, although other stabilization methods, such as freezing, may be appropriate for some types of samples. Suitable fixing media include commercially available resins or waxes. Other materials and encapsulation techniques used for biological samples may also be applicable, although these techniques may require significant adaptation to achieve meaningful results on friable inorganic sample materials. An optional image of the outside of the sample can be obtained before or after preparation of the sample (step 44).

The system then performs a first active exploration of a region of the sample (step 46). This step preferably involves cutting the sample, but other approaches that expose a portion of the inside of the sample could also be used instead of, or in addition to, cutting, such as ablation, milling, etching, or selective chemical treatments. In the embodiment shown, the actuator 24 moves the blade 20 with respect to the processing surface 20. This causes the blade to ride along adjustable cutting guides to remove a thin slice from the top of the sample to expose an inner surface below.

The system then acquires a hyperspectral image of the exposed inner surface (step 48). The process of exploring and acquiring can be repeated for successive slices (steps 46, 48, and 50), until sufficient chemical information has been acquired, or the sample has been exhausted. The acquired data can be processed and/or evaluated as it is acquired, and/or at the end of the process (step 52). Evaluation can include the use of a variety of spectral techniques that are well known in the art for investigative, formulation-phase, quality control, or root cause analysis purposes. An important application of the technique is to understand the uniformity of mixing of ingredients in the sample, but other information, such as the presence of buried contaminants may also be sought. Techniques pertinent to the analysis of the spatial distribution of ingredients is described in "Pattern Recognition in Hybrid Spatial-Spectral Space" and "Spectrometric Process Monitoring," serial Nos. 60/343,691, and 60/394,053, filed on Dec. 21, 2001 and Jul. 3, 2002, respectively, which are herein incorporated by reference.

Preferably, the overall data set obtained from the process will be a four-dimensional multispectral data hypercube. This hypercube will include spectral information for a number of different wavelengths for each of a series of voxels in a set of stacked x-y planes that pass through the sample and offset from each other in the z-direction. In some applications, however, even a single interior image may be sufficient. And fully populated two-dimensional images in each plane might not be needed in all instances. Moreover, spectral information from only a few wavelengths or even a single wavelength may be sufficient in some applications. While the whole data hypercube is preferable, therefore, one that only exhibits a single value in one or more of the four dimensions (x, y, z, λ) may also be useful in some instances.

The selection of the spatial resolution in the z-direction (i.e., the slice thickness) may be made in view of the spatial resolution of the array (i.e., the effective pixel size). This can allow optimum distribution of the acquired voxels. If the spatial resolution of the z-direction acquisitions does not have a relationship to the spatial resolution of the array that is acceptable to the user, values from adjacent planes can be interpolated to obtain an interpolated plane set that bears an acceptable relationship to the spatial resolution.

The exploration subsystem is preferably operative within the field of view of the acquisition subsystem. This allows for the unattended automatic acquisition, or at least efficient semiautomatic acquisition, of a whole four-dimensional data set for a sample. It can also help to ensure consistent optical alignment between the subsystems during the acquisition. To this end, the exploration subsystem and acquisition subsystem can be permanently mechanically attached to form a dedicated instrument, with the sample being constrained within the instrument in at least one dimension. Permanent electrical and digital links can also be provided. Systems in which the two subsystems are only temporarily linked can also be built, so that the two subsystems can be used separately. And it may even make sense in some instances to perform some or all of the exploration steps outside of the field of view of the acquisition system.

Where the system is a dedicated instrument, it can be operated by a single control and analysis system 36, which can be computer-based. This system can coordinate the various control and analysis functions of the sample processing subsystem 12 and the acquisition subsystem 14. This approach can yield a system that permits highly automated operation. For example, the system could be designed to section a sample, acquire images of its interior, and display a corresponding result in response to a single user command. Of course, control and analysis of these functions can also be distributed into separate systems, and/or performed manually.

One or more reference indices can be embedded with the sample. These can serve as a spatial reference points to enhance alignment. They may also include appropriate reference materials to allow for calibration and/or differential measurements.

EXAMPLE 1

Figure 3:
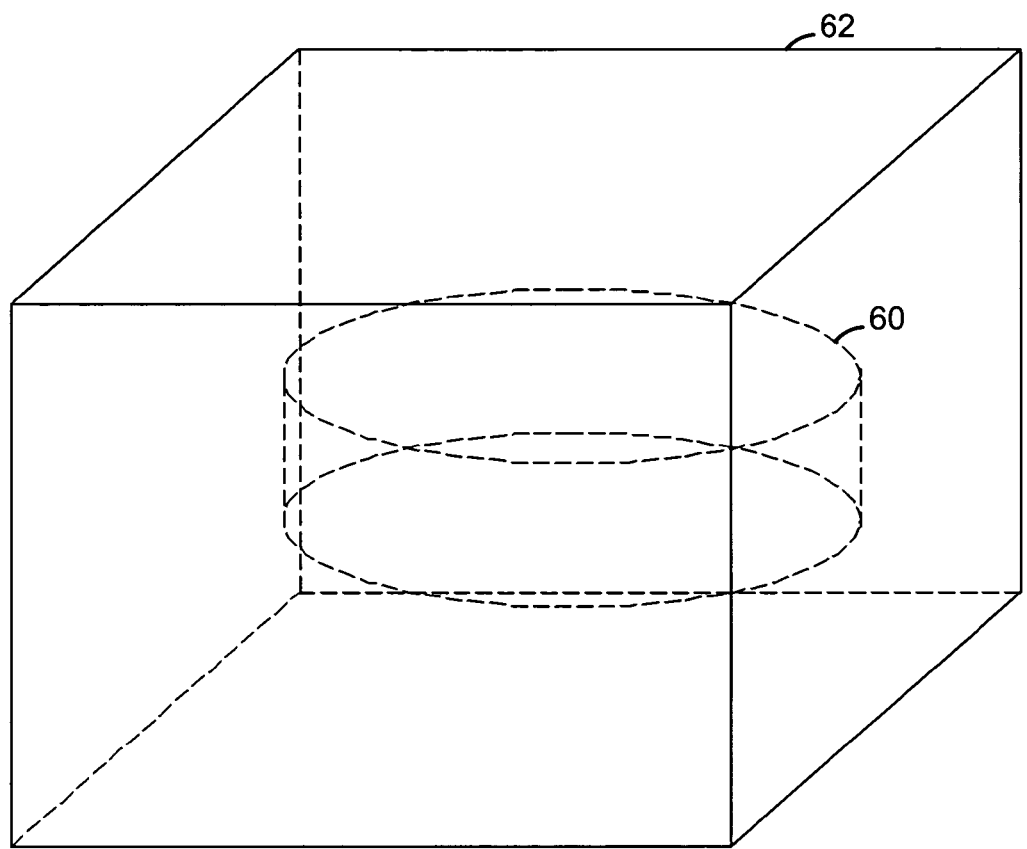
FIG. 3 is diagrammatic perspective sketch generally illustrating the preparation of a pharmaceutical tablet for use in the system of FIG. 1.
Figure 4:
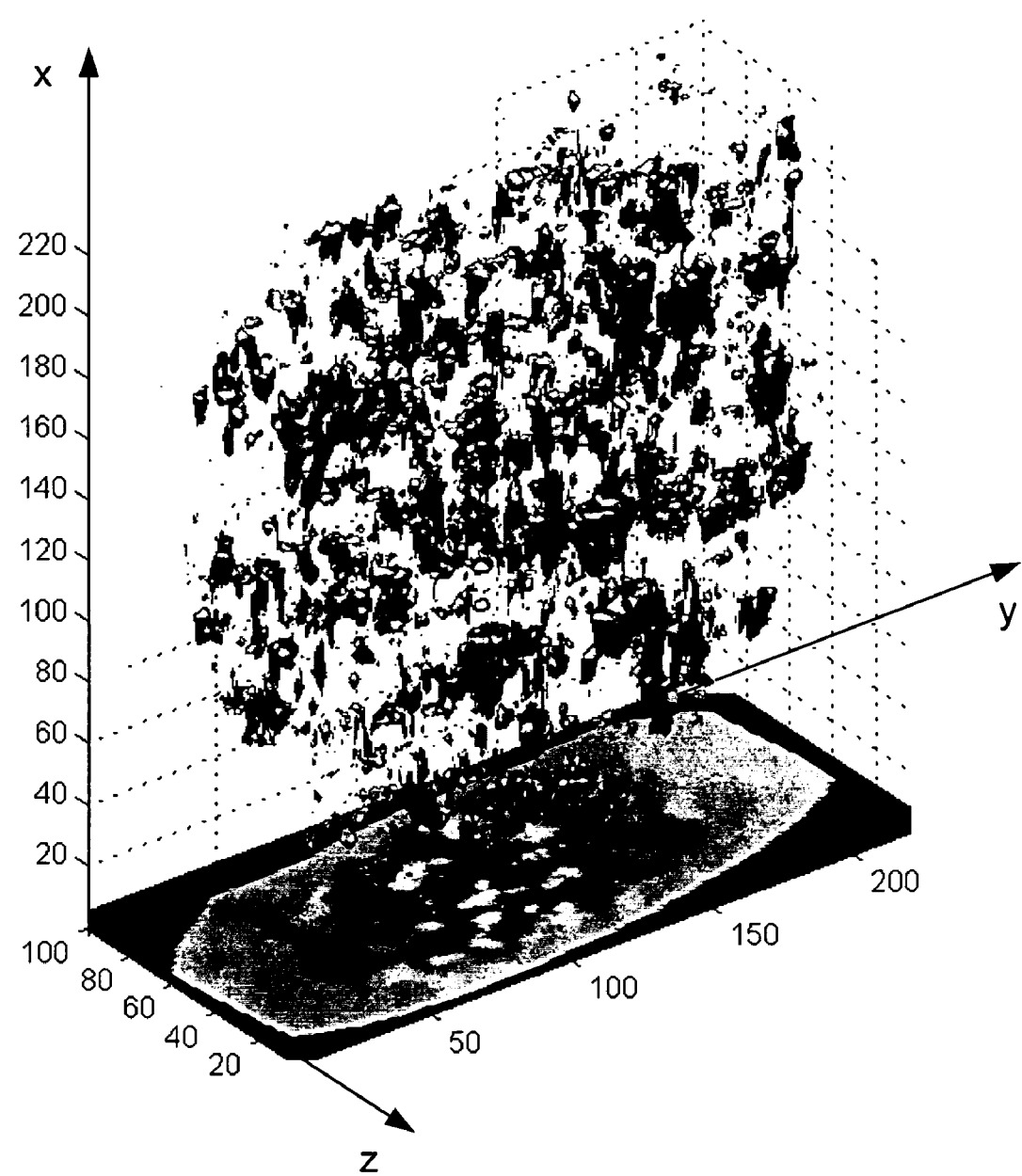
FIG. 4 is a three-dimensional plot of the spectral response of an acetaminophen tablet acquired by a system similar to that shown in FIG. 1.

Referring to FIGS. 3 and 4, a tablet 60 made up of acetaminophen (20%) and a mixture of excipients (80%) was encased in a block of high-temperature holding wax 62, which was obtained from the Universal Shellac And Supply Company. The compound sample was cut about 40 times at 30 micron intervals to reveal a corresponding number of x-y planes inside the sample using a standard laboratory razor blade, and a micrometer obtained from Mitutoyo, of Japan.

A three-dimensional multispectral image cube was obtained after each cutting operation. Each of these cubes were then converted to one-pixel deep chemical images by comparing a set threshold with the amplitude of light absorbed by the sample at a single wavelength corresponding to an absorption band of acetaminophen. The planes were then plotted in a volumetric plot 70. This example reveals that the use of embedded exploration techniques coupled with the acquisition of spectral information can provide a substantial amount of information about the distribution of active ingredients in friable objects such as pharmaceutical tablets.

While this example used a sample that is well suited to detection with a single wavelength, more complex spectral signatures could be accommodated using well-known multivariate methods. And while only the acetaminophen is shown in this example, it is also possible to provide an image that also plots chemical data for one or more additional ingredients. These multi-ingredient plots can employ different colors to represent different chemical species, and can convey a substantial amount of information about the chemical distribution within a sample.

In another experimental embodiment, a simple rotary blade was used instead of a razor blade to cut the sample. A vacuum collection system was also provided to collect airborne particles that could be released by the cutting operation. This embodiment was used successfully to obtain volumetric images of a number of different types of samples embedded in the holding wax, ranging from pharmaceutical tablets to corn kernels.

In the above-described embodiment, the cutting surface 18 is presented as being preferably stationary with cutting taking place in the field of view of the acquisition system to allow for successive acquisitions of the sample as material is being removed from it. It is of course also possible to look at the removed material in transmission. For example, a compound mechanism in the system could remove successive slices using a microtome and then move them between a source and sensor to obtain a series of transmission images.

The present invention has now been described in connection with a number of specific embodiments thereof. However, numerous modifications which are contemplated as falling within the scope of the present invention should now be apparent to those skilled in the art. It is therefore intended that the scope of the present invention be limited only by the scope of the claims appended hereto. In addition, the order of presentation of the claims should not be construed to limit the scope of any particular term in the claims.

What is claimed is:

1. A spectral acquisition apparatus, comprising:
   an exploration subsystem operative to repeatedly expose different interior portions of a three-dimensional sample while the sample remains in a same position, wherein the exploration subsystem includes a cutting implement and a guide,
   a spectral acquisition subsystem operative to acquire images of each of the interior portions exposed by the exploration subsystem: while the sample remains in the same position, wherein the exploration subsystem is operative in the field of view of the spectral acquisition system, and
   a control module operative to control the exploration subsystem, and an analysis module for assembling the acquired spectral images into a three-dimensional data representation that includes spectral information for positions in three spatial dimensions.

2. The apparatus of claim 1 wherein the exploration subsystem includes an actuator operative to advance the cutting implement.

3. The apparatus of claim 1 further including a mechanical link, an electrical link, and a digital link between the exploration subsystem and the spectral acquisition system.

4. The apparatus of claim 1 wherein the spectral acquisition system includes a two-dimensional array detector and a spectrally selective device.

5. The apparatus of claim 1 wherein the spectral acquisition subsystem operates in near-infrared or mid-infrared spectral regions.

6. The apparatus of claim 1 further including an airborne waste collection system having an inlet proximate the exploration subsystem.

7. The apparatus of claim 1 wherein the exploration subsystem includes a sample embedding substance.

8. A spectral acquisition method, comprising:
   repeatedly actively processing a sample to expose characteristics of interior portions of the sample in a series of steps of processing while the sample remains in a same position,
   acquiring spectral information from the interior portions of the sample exposed in each of the steps of processing while the sample remains in the same position, wherein the steps of actively processing and acquiring are applied to a friable material,
   preparing the friable material to withstand the step of actively processing before the step of actively processing, wherein the step of preparing includes fixing the sample in a fixing material and the step of actively processing includes cutting the sample, and
   assembling the acqiuired spectral information into a three-dimensional data representation that includes spectral information for positions in three spatial dimensions.

9. The method of claim 8 wherein the steps of preparing, actively processing, and acquiring are applied to a bulk pharmaceutical material.

10. The method of claim 8 wherein the steps of preparing, actively processing, and acquiring are applied to a pharmaceutical dosage unit.

11. The method of claim 8 wherein the steps of preparing, actively processing, and acquiring are applied to a pharmaceutical tablet including at least one active ingredient and one inert ingredient.

12. The method of claim 8 further including a step of selecting a spatial separation between the steps of actively processing to be on the same order as that of a spatial resolution of the step of acquiring.

13. The method of claim 8 further including a step of interpolating data received from the steps of acquiring to adjust for a spatial separation between the steps of actively processing.

14. The method of claim 8 wherein the steps of actively processing expose planar interior surfaces.

15. The method of claim 8 wherein the step of actively processing and the step of acquiring both take place as part of an automated sequence.

16. A spectral acquisition method, comprising:
    actively processing a sample to expose characteristics of interior portions of the sample while the sample remains at a same position in a series of steps of actively processing,
    acquiring spectral information from the interior portions of the sample exposed in the steps of actively processing while the sample remains at the same position, and
    processing the spectral information acquired in the step of acquiring to obtain two-dimensional chemical image planes and reconstructing at least one three-dimensional image from the two dimensional chemical image planes.

17. The method of claim 16 wherein the steps of actively processing and acquiring are applied to a friable material and further including the step of preparing the friable material to withstand the step of actively processing before the step of actively processing.

18. The method of claim 16 wherein the step of acquiring operates in near-infrared or mid-infrared spectral regions.

19. A spectral acquisition apparatus, comprising:
    means for holding a friable pharmaceutical tablet,
    means for repeatedly exposing interior portions of the friable pharmaceutical tablet while the friable pharmaceutical tablet remains in a same position, wherein the means for exposing includes a cutting implement and a guide,
    means for repeatedly obtaining spectral images of the exposed interior portions: while the friable pharmaceutical tablet remains in the same position, wherein the means for repeatedly obtaining is operative to obtain a set of images of the exposed interior portions of the tablet, and
    means for assembling the obtained spectral images into a three-dimensional data representation that includes spectral information for positions in three spatial dimensions.

20. The apparatus of claim 19 wherein the means for holding include means for embedding the pharmaceutical tablet.

21. The apparatus of claim 19 wherein the means for holding include a holding wax.

22. The apparatus of claim 19 wherein the means for exposing includes means for advancing the cutting implement.

23. The apparatus of claim 19 wherein the means for holding are operative to hold the pharmaceutical tablet in a field of view of the means for obtaining spectral images during operation of the means for exposing.

24. The apparatus of claim 19 further including a mechanical link, an electrical link, and a digital link between the means for exposing and the means for obtaining spectral images.

25. The apparatus of claim 19 further including means for controlling the means for exposing and for processing information from the means for obtaining spectral images.

26. The apparatus of claim 19 wherein the means for obtaining spectral images operate in near-infrared or mid-infrared spectral regions.

27. The apparatus of claim 19 further including means for collecting airborne waste from the means for exposing.

28. A spectral acquisition method comprising,
positioning a pharmaceutical tablet at a first position within an optical field of view of an acquisition system,
removing material from the tablet while the tablet remains at the first position within the field of view,
acquiring a first spectral image of the tablet by the acquisition system after the step of removing, while the tablet remains at the first position within the field of view,
removing further material from the tablet while the tablet remains at the first position within the field of view in one or more further steps of removing,
acquiring a further spectral image of the tablet by the acquisition system after each further step of removing, while the tablet remains at the first position within the field of view, and
assembling the acquired spectral images into a three-dimensional data representation that includes spectral information for positions in three spatial dimensions.

29. The method of claim 28 wherein the steps of removing and acquiring are applied to a friable tablet and further including the step of preparing the friable tablet to withstand the step of removing.

30. The method of claim 29 wherein the steps of preparing, removing, and acquiring are applied to a pharmaceutical tablet including at least one active ingredient and one inert ingredient.

31. The method of claim 29 wherein the step of preparing includes fixing the sample in a fixing material and the step of removing includes cutting the sample.

32. The method of claim 29 wherein the step of preparing includes fixing the sample in a fixing material and the step of removing includes cutting the sample with a blade.

33. The method of claim 29 wherein the step of preparing includes fixing the sample in a fixing material and the step of removing includes cutting the sample with a rotating blade.

34. The method of claim 28 further including a step of selecting a spatial separation between the steps of removing to be on the same order as that of a spatial resolution of the step of acquiring.

35. The method of claim 28 further including a step of interpolating data received from the steps of acquiring to adjust for a spatial separation between the steps of removing.

36. The method of claim 28 wherein the step of removing and the step of acquiring both take place with the sample in a position constrained in at least one dimension.

37. The method of claim 28 wherein the step of removing and the step of acquiring both take place as part of an automated sequence.

38. The method of claim 28 further including the step of obtaining the tablet as a sample of a tablet making process and wherein the steps of obtaining, removing, and acquiring take place as part of a quality control process for the tablet making process that includes further steps of obtaining, removing, and acquiring.

39. The method of claim 28 further including the step of obtaining the tablet from a formulation-phase experiment.

40. The method of claim 28 wherein the steps of removing and acquiring take place as part of a root-cause analysis process.

41. The method of claim 28 wherein the step of acquiring an image acquires an image in near-infrared or mid-infrared spectral regions.

42. The method of claim 28 wherein the step of acquiring is operative to obtain an image reflected from a surface of the tablet exposed by the step of removing.

43. The method of claim 8 wherein the step of acquiring operates in near-infrared or mid-infrared spectral regions.

* * * * *